Figure 3:
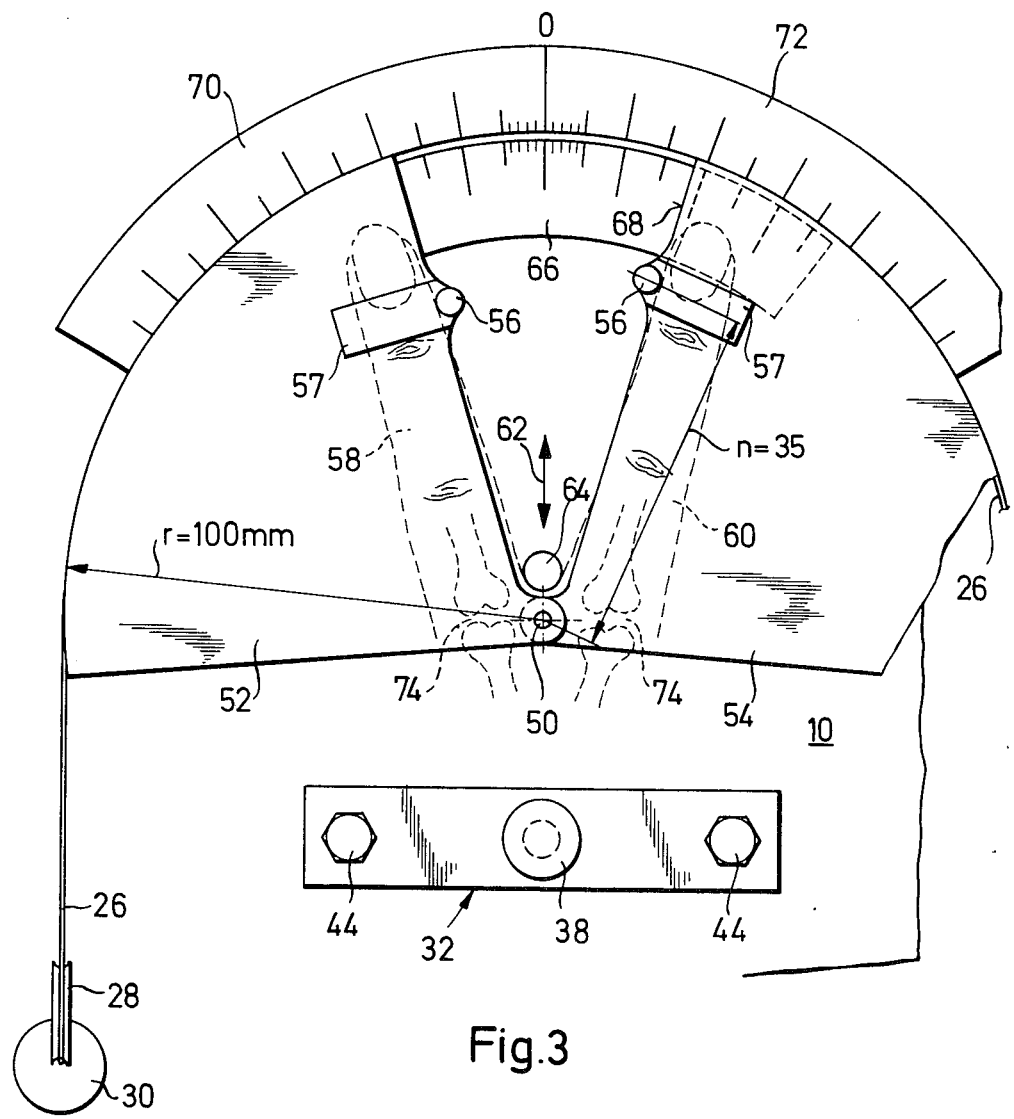

United States Patent [19]

Wagner

[11] 4,037,480
[45] July 26, 1977

[54] MANUAL DEXTERITY APTITUDE TESTING

[75] Inventor: Christoph Wagner, Dortmund-Kirchhorde, Germany

[73] Assignee: Max-Planck-Gesellschaft zur Forderung der Wissenschaften e.v., Gottingen, Germany

[21] Appl. No.: 606,725

[22] Filed: Aug. 21, 1975

Related U.S. Application Data

[63] Continuation of Ser. No. 403,956, Oct. 5, 1973, abandoned.

[30] Foreign Application Priority Data

Oct. 7, 1972 Germany ............................ 2249208

[51] Int. Cl.² .............................................. A61B 5/00
[52] U.S. Cl. .................................... 73/432 R; 128/2 S
[58] Field of Search ................... 73/432 R, 379, 381; 128/2 S, 26; 33/174 D

[56] References Cited

U.S. PATENT DOCUMENTS 3,680,386  8/1972  Cannon ............................... 128/2 S

FOREIGN PATENT DOCUMENTS 219,076  1968  U.S.S.R. .............................. 128/2 S

OTHER PUBLICATIONS

Goddard, et al., "The Measurement of Stiffness in Human Joints," Apr. 17-19, 1968, pp. 229-234.
Dickson, et al., "A Device for Measuring the Force of the Digits of the Hand," July 1972, pp. 270-273.

Primary Examiner—James J. Gill
Assistant Examiner—Anthony V. Ciarlante
Attorney, Agent, or Firm—Brisebois & Kruger

[57] ABSTRACT

Method and apparatus for testing the aptitude of a person for an activity requiring manual dexterity according to which a joint in an arm of the person is subjected to a predetermined stress in a direction in which the joint moves, and the resulting deflection is measured.

17 Claims, 8 Drawing Figures

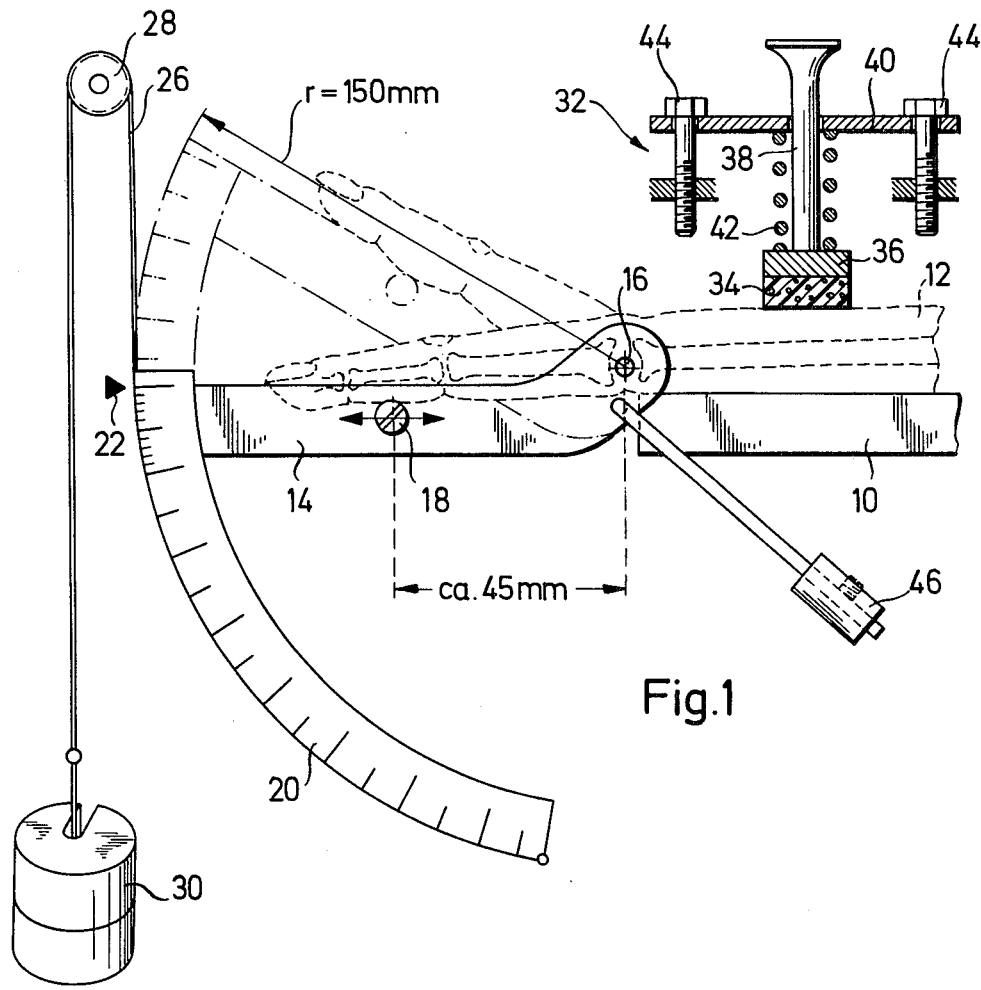

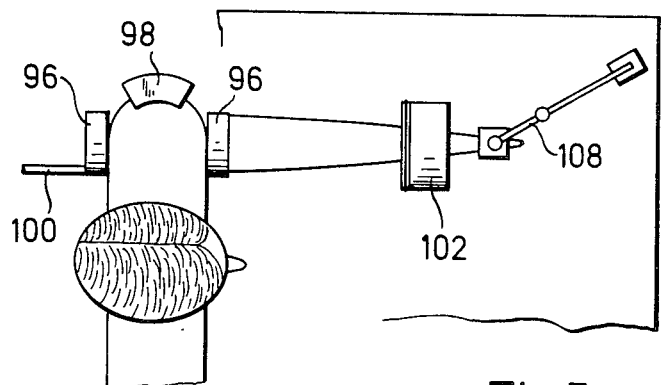
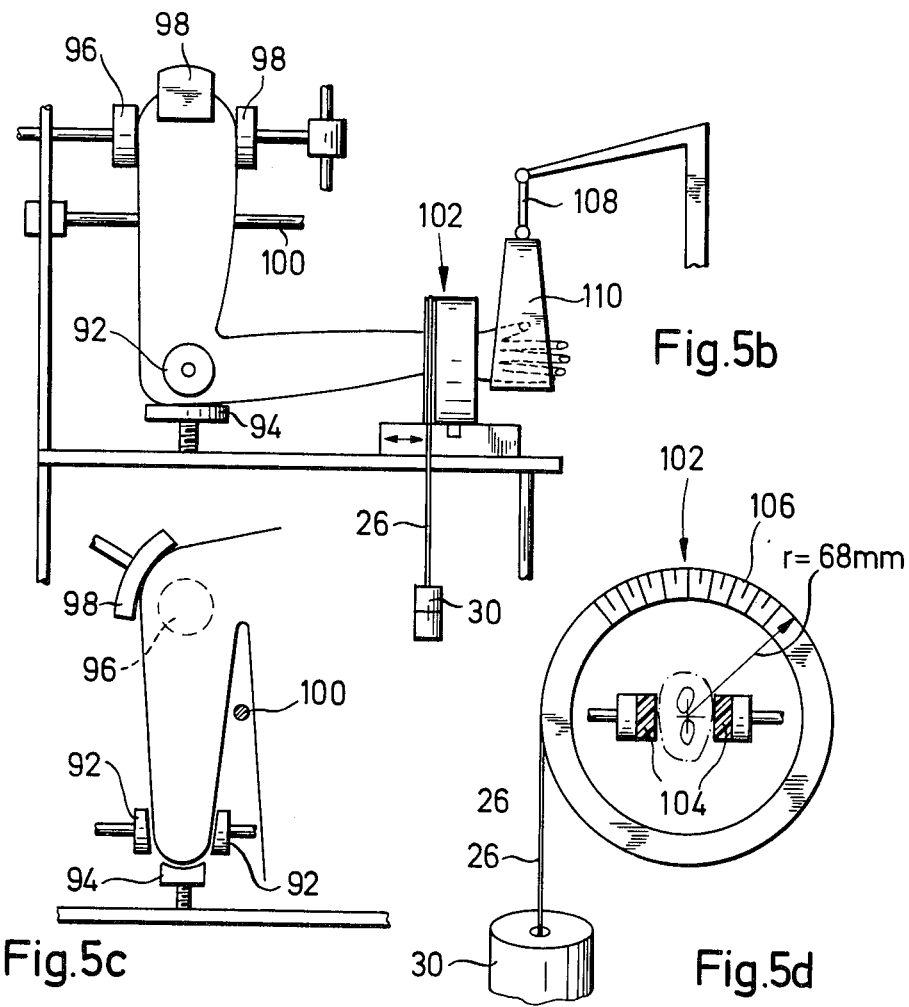
Fig.5a
Fig.5b
Fig.5c
Fig.5d

MANUAL DEXTERITY APTITUDE TESTING

This is a continuation of application Ser. No. 403,956, filed Oct. 5, 1973 now abandoned.

The present invention concerns procedures and devices for the testing of a person's aptitude for an activity requiring manual dexterity.

In order to be able to achieve maximum performances or even only good performances for a longer period, not only talent and inclination must be present for many professions and activities, but relevant physical preconditions must also be fulfilled. This can be demonstrated, particular for violinists and pianists, by investigations on which the present invention is based; similar conditions do, however, obtain also in the case of other activities and professions, as for instance in the case of shorthand typists, punch-card operators and similar professions.

It is obvious that the choice of such a profession could be made easier and that wrong decisions could be avoided if it were possible to determine objectively the physical aptitude of the person in question before the commencement of training.

The present invention has the aim of achieving this possibility.

According to the invention, this objective is solved by the fact that at least one joint system of at least one arm of the person in question is subjected to a stress acting in the direction of one degree of freedom of movement of the joint system, and that the magnitude of the resulting deflection of the joint system is then measured. The measurement is preferably carried out on several joint systems. The values obtained are a safe basis for the assessment of the aptitude of the person in question.

Figure 4:
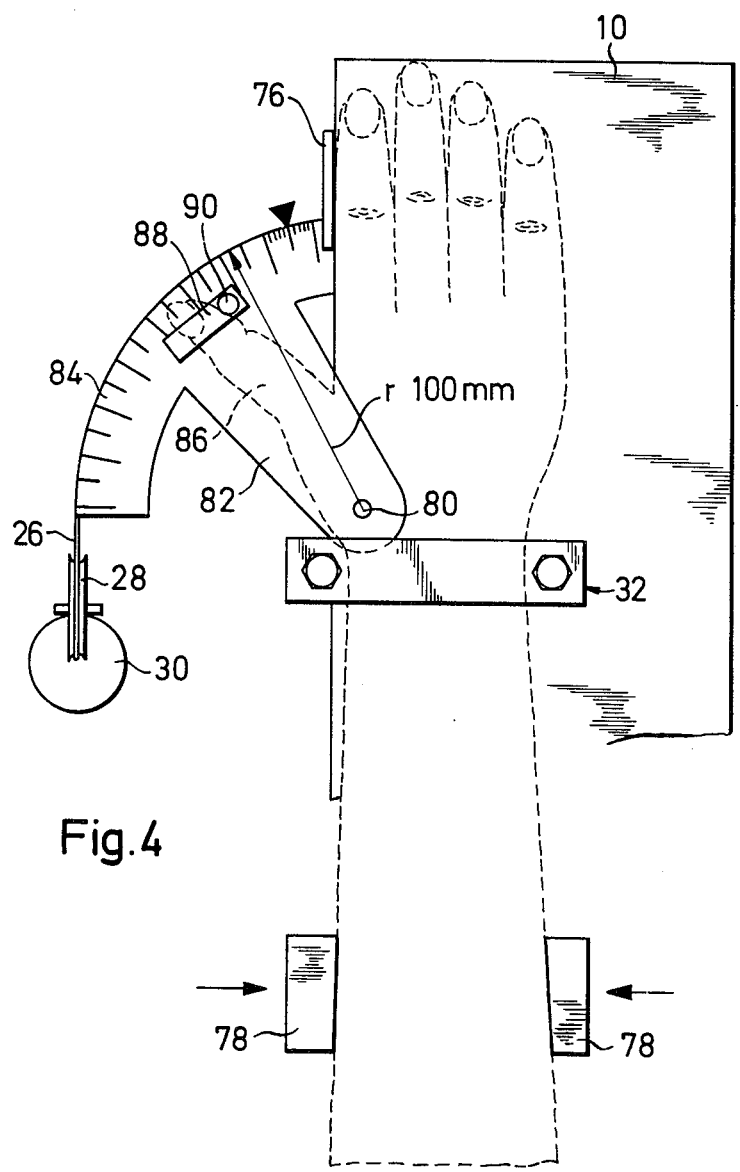

The idea of the invention, further developments and extension of the invention as well as devices for carrying out the procedure according to the invention are explained in more detail in the following with reference to the drawings in which embodiments of devices according to the invention are shown schematically; the figures show:

FIG. 1 a schematic drawing of a device for the measurement of the measurement of the hyperdistensibility of the fingers in the metacarpo-phalangeal joint;

FIG. 2 a plan view of a part of the device according to FIG. 1;

FIG. 3 a schematic plan view of a device for the measurement of the splayability of the fingers;

FIG. 4 a plan view of a device for the measurement of the splay angle of the thumb; and FIG. 5 a device for the measurement of the extent of rotatability of the lower arm.

The devices described in the following can be used for passive and also for active measurements. In the case of an active measurement, the measured parameter is produced by the muscular force of the test subject, whereas in the case of passive movements it is produced by a force exerted from outside without active participation of the person tested. It was found that the values obtained by passive measurement give considerably more information than the values measured upon active participation of the person tested.

The device shown in FIG. 1 and 2 serves for the measurement of the hyperdistension of the fingers in the metacarpo-phalangeal joint or, in other words, of the angle by which the four fingers with the exception of the thumb can be bent upwards in relation to the metacarpus. The device contains a table with a level plate 10 on which the hand 12 of the test subject rests during the test with the back of his/her hand showing upward. A swivelling frame 14 is attached to the table-top 10 by means of a joint, the swivel axis 16 in the embodiment shown lying a little outside the edge of the table-top. At the frame 14, a transversely extending rod 18 is attached which can be moved in the direction of the double arrow and which supports the fingers in the region of the distal or middle finger segment during the test. At the front end of the frame an angle scale 20 is attached which acts together with a fixed mark 22. The angle scale has at its outer end a groove 24 which holds a cord 26 fixed at the lower end of the anle scale (or a wire or similar) which is led over a pulley 28 and which is connected at the other end to a weight 30.

An attachment 32 for the fixation of the hand during the measurement is fitted to the table. The attachment contains a pressure beam 36, preferably slightly concave in the downwards direction and fitted with a rubber cushion 34, to which two rods 38 are fitted which are guided in the guides 40. One compression spring 42 each is provided for between the guides 40 and the pressure beam. The guides 40 can be pressed downwards by stretching devices, indicated only schematically, so that the pressure beam 36 is pressed by the compression springs 42 with a predetermined force against the back of the hand 12.

For the measurement, the hand of the test subject is clamped in such a way that the swivel axis 16 is at least approximately in line with the articular space between the metacarpal bones and the first segment of the fingers, as is shown in FIG. 1 by the bones indicated by a dotted line. The distance between the swivel axis 16 and the rod 18 is adjusted to a prescribed value, and subsequently a weight 30 of prescribed magnitude is attached to the cord 26. The frame 14 is balanced with respect to the swivel axis 16 by counterweights in such a way that the torque acting on the fingers is determined exclusively by the weight 30. The frame is pulled upwards by the weight 30, e.g. into the position indicated by the dotted line, and the fingers are overextended, i.e. bent backwards in the direction towards the back of the hand. The hyperdistension angle resulting from a certain stress which can be read off the angle scale 20 by means of the mark 22 is an important criterion for the subject's aptitude to be a pianist or violinist. With a distance of 45 mm between the swivel axis 16 and the rod 18, a distance of 150 mm between the swivel axis and the point of application of the force exerted on the frame 14 by the weight 30, and a weight 30 of 500 g, the median value of the left hand of about one hundred professional violinists was 32°, with 80% of the values lying between 19° and 44°. It was found that with small hyperdistension angles, there was a considerably more pronounced tendency to tendovaginitis and other consequences of overstraining than in people with a greater angle of hyperdistension. A constitutionally small angle of hyperdistension can apparently not be increased even by exercise or training.

The device shown schematically in FIG. 3 serves for the measurement of the splayability of the fingers with the exception of the thumb. Both, the splay angle between a splayed finger and a reference line (which is normally placed in the middle between the finger measured and the adjoining finger when these two fingers touch each other and are in resting position) and also the splay angle between two adjoining fingers can be measured. Here too, the determination of the passive splay is of particular importance, i.e. the determination of the splay angle resulting from the effect of an external force of a prescribed magnitude.

The device according to FIG. 3 again contains a table with a level plate 10 on which the hand to be tested is placed with the back showing upwards and onto which it is then fixed with an attachment 32. The attachment 32, only sketched in FIG. 3, can be constructed in the same way as the attachment 32 of the apparatus shown in FIG. 1. However, one can also use a simple clamp since here it is not necessary to press the hand against the top of the table with an exactly defined force.

Two sector plates 52 and 54, revolving around a common axis 50 running vertically to the plate 10, are positioned at the plate 10 or at the frame (not illustrated) of the device according to FIG. 3. The sector plates carry raised small rolls or pins 56 which serve as a depression for either finger 58 or 60 and which are fitted with a rim 57 for the finger in question. Furthermore, a rod 64, moveable in the direction of the double arrow 62, is attached to the frame or the plate 10. To one of the two sector plates, e.g. the sector plate 52, an angle scale 66 is attached for which one edge 68 of the other sector plate 54 serves as reading mark. Apart from this, two fixed angle scales 70, 72 which are connected to the frame or plate 10 are provided for, from which the angle of rotation of the sector plates 52 and 54 can be read.

Similarly to the angle scale 20 in FIG. 1, the sector plates 52 and 54 are each fitted at the circumference with a slot not shown in FIG. 3 which carries a cord 26 which, as in the device according to FIG. 1, is led over a pulley 28 and connected to a weight 30.

The hand to be tested is pressed against the plate 10 by means of the attachment 32 in such a way that the connecting line of the articular space 74 between the metacarpal bone and the bone of the next finger segment of the finger to be tested and of the adjoining finger runs through the extrapolation axis, 50. Subsequently, the rod 64 is pushed in the direction of the plate 10 until it lies against the hand and is then fixed. Apart from fixing the metacarpus by means of the attachment 32, this measure contributes to preventing deflections of the hand through which the measurements could be falsified. The fingers 58 and 60 are then lying closely to the sides of the rods 56, with their sides facing each other. With the fingers closed, the middle line between the two fingers should point to zero on the scales 70 and 72.

Now, a weight 30 of prescribed magnitude is attached to the cord 26 by which the sector plate 52 or 54 respectively is swivelled around the axis 50 and by which the corresponding finger, e.g. 58, is splayed by the corresponding pin 56. The angle of splay for the finger 58 can then be read off the scale 70. When the two fingers 58 and 60 are splayed in the way described, the total angle of splay between these two fingers can then be read off the scale 66.

The splay angles between two fingers can have very different values even on the same hand. A great splaying ability is of great importance particularly for violinists, since it is an essential precondition for a relatively easy playing of fast passages. A movement during which the particular muscle is under full stress requires namely unproportionally more time than a movement which requires only a medium muscle stress.

For the left hand of male professional violinists, for instance, 80% of all values of splay between fingers 2 and 3 (index and middle finger) lay between 27° and 46°, with a median value of 32°; the median value of splay between fingers 3 and 4 was 27° and for splay between fingers 4 and 5, the median value was 38°.

The device shown in FIG. 4 serves for the measurement of the splayability of the thumb. In principle, its construction is similar to that of the device according to FIG. 3 and contains a table with a plate 10 on which the hand and the lower arm of the test subject are placed in such a way that the outer side of the index finger lies closely against a plate-fixture 76 attached to the edge of the table. The wrist joint is pressed against the plate 10 by means of an attachment 32 which can be constructed in the same way as the attachment 32 on the arrangements according to FIG. 1 and 3. The lower arm is secured on the plate by two contact jaws 78 which can be kept under compression to prevent deflection movements.

Below the plate 10, a component is positioned which can be swivelled around an axis 80 running vertically to the plate 10 and which, similarly to the sector plates 52 and 54, is fitted with an angle scale 84 the outside of which has a slot for a cord 26. Again, the cord 26 runs over a guide pulley 28 and is connected to a weight 30 so that the component 82 can be turned by means of a defined force and exerts a predetermined torque on the thumb 86 of the hand which rests on a rest 88 rising from component 84 and lies closely against a stop pin 90. The hand of the test subject is clamped in such a way that the extrapolation axis 80 runs through the articular space between the metacarpel bone of the thumb and the greater multangulm of the hand. The measurement is then carried out as with the device according to FIG. 3.

The device shown in FIG. 5 serves for the measurement of the rotatability of the lower arm which is of importance mainly for violinists. With this device too, both active and passive measurements can be carried out as with the previously described devices, with the passive measurements again being of greater significance.

The device according to FIG. 5 consists in principle of an arrangement for the fixation of the elbow and the upper arm of the test subject (in order to prevent deflection movements) and an arrangement by means of which a torque acting around the axis of the lower arm and of predetermined value can be exerted on the lower arm in the region of the wrist joint.

The fixation of the elbow is effected by two contact jaws 92 which can be pressed against the sides and a vertically adjustable fixture 94 (FIG. 5b and c). The fixation of the upper arm is effected by two contact jaws 96 which are positioned to the front and back of the shoulder region of the test subject (FIG. 5a), and a curved fixture 98 which prevents a displacement of the shoulder upwards or outwards. Furthermore, an adjustable and securable rod 100 is provided which runs between the upper part of the body and the upper arm of the test subject and which lies closely against the inner side of the upper arm so that a medial deflection of the upper arm is prevented. The measuring device proper is designated 102, and contains two contact jaws 104 (FIG. 5d) by means of which the wrist joint can be clamped with a prescribed force. The clamping device containing the contact jaws 104 can be constructed in a similar way as had been explained by means of the arrangement 32 of the device according to FIG. 1. The contact jaws 104 can be swivelled around a ball joint, not shown, and connected to an angle scale 106 which again has a slot on its outer side in which runs a cord 26 fitted with a weight 30. A sling 110, into which the hand protruding from the measuring fixture 102 is placed, is hung from a stand 108 in front of the measuring fixture 102.

The measuring fixture 102 is adjustable in the direction of the axis of the lower arm. All other parts of the device which act together with the test subject are also adjustable in such a way that persons of different body height and different proportions can be tested.

To carry out a test, the arm to be investigated is pushed through the measuring fixture 102 and the device is adjusted in such a way that the various parts come into the desired position with respect to the test subject. Subsequently, the elbow is placed on the fixture 94 and clamped in by means of the contact jaws 96, the fixture 98 and the rod 100. The hand is placed in the sling 110 and this is adjusted in such a way that the hand rests quite relaxed in the sling 110. Finally, the wrist joint is clamped in with defined compressive force between the contact jaws 104.

In order to measure the active rotatability of the lower arm, one asks the test subject to rotate his/her hand as far as possible towards the inner and the outer side and the resulting angles are read off the angle scale 106. For the measurement of the passive rotatability of the lower arm, a weight 30 with a prescribed value (e.g. 500 g) is hung on the cord 26, and the angle of rotation resulting upon relaxation of the muscles is measured. In the case of the left hand of male violinists, 80% of the values lay between 56° and 100°, with a median value of 86°. In this case, the weight was 500 g, and the radius of the slot in which the cord 26 ran, was about 68mm.

The rotatability of the hand as a whole around the longitudinal axis of the lower arm can therefore be measured with the device according to FIG. 5. However, important statements can also be made on the basis of the results of the corresponding investigation of the other two degrees of freedom of movement of the hand as a whole, i.e. the rotatability of the hand upward and downward and the rotatability of the hand as a whole in the lateral direction. The device, not shown, for the measurement of the movability in these two degrees of freedom preferably contains a plate on which the lower arm is fixed, and a movable holder for the hand. This movable holder can be swivelled around an axis which runs in the plane of ulna and radius or, respectivel, vertically to this plane through the corresponding centres of rotation, i.e. roughly through the area of the lunate bone.

The device according to FIG. 1 can be altered without difficulty in such a way that the hyperdistensibility of the fingers 2 to 5 (index finger to small finger) can be measured individually. In this case, a holder for an individual finger is then provided for instead of the rod 18. According to an embodiment of this device for the measurement of the hyperdistensiblitiy of individual fingers, devices are provided by which the fingers adjoining the finger to be tested for its hyperdistensibility can be fixed in a predetermined position.

One can therefore measure the hyperdistension of the individual fingers both with the remaining fingers being relaxed and hanging down and also with the adjoining fingers being in a well defined position; in this way the 'problem of the fourth finger', famed and notorious with pianists, can be determined objectively.

The device according to FIG. 3 can be altered in such a way that the active or passive lateral movement of each individual finger can be measured. For this purpose, the adjoining fingers can either hang down loosely or be fixed in certain positions. The finger whose movability in lateral direction is to be measured is clamped in on both sides, e.g. between two rods similar to the rods 56 in FIG. 3, and for the active measurement one determines the angle by which the finger in question can be swung to and fro. For passive measurements, a prescribed force is exerted, first in one direction and then in the other direction, similar to the device according to FIG. 3, with the torque caused by the force having to act round an axis which runs through the articular space between the metacarpal bones and the bones of the adjoining finger segment of the finger in question.

With all devices, the point of application of the forces of torques are preferably adjustable. For instance, the rod 18 is adjustable in the direction of the double arrow, (FIG. 2). The rods 56 can be adjustable in radial direction. The corresponding applies for the stop pin 90 and fixture 88 (FIG. 4).

The above mentioned measurements, i.e. the measurement of the movability of the various joint systems during movements caused by the muscle force of the person in question, can be supplemented, according to a further extension of the present invention, in that one measures the forces which the person in question has to exert for this. The actual capabilities are namely limited, on the one hand by constitutional characteristics of the joint system which can be determined with the above described passive measurements. On the other hand, a limit is set by the forces which the muscle effecting the movements in question are able to exert.

The muscle force can preferably be measured by asking the person in question to exert a force in the direction of the particular degree of freedom in various positions of the corresponding joint system, and by then evaluating the force values found for various positions, e.g. by graphical extrapolation. This will be explained by means of the example of the splaying of the fingers:

One finger, e.g. the index finger, is clamped in a holder which forms the input member of a force meter. The force meter can, for instance, contain a strain gauge, a piezoelectric crystal or similar, and be constructed in known fashion. The fingers 3 to 5 (middle finger to little finger) hang down loosely. The metacarpus is fixed as usual. Now one asks the person in question to move the index finger right or left (in the plane of the hand) with all his/her strength. The force thus exerted is measured. Now the index finger is brought into a position slightly away from the middle finger, and the person in question is asked to splay the index finger further outside with all his/her strength. These measurements are repeated for several splay angles on both sides of the resting position. The splaying force which the person in question is able to exert on the force meter decreases the more the finger is splayed away in the measuring position from the resting position. At the maximal, actively reached splay angle, this force becomes nil. The course and shape of the curve permit important deductions with regard to the forces which the person in question is able to exert upon various positions of that particular finger. The above described measurements of force can also be carried out for various positions of the adjoining finger. Measurements of the dependence of the exerted force on the position of the corresponding, force-exerting part of the body can, of course, also be carried out for other joint systems and degrees of freedom, particularly the degrees of freedom of joint systems described above in FIG. 1 to 5.

I claim:

1. An apparatus for testing a joint system between two relatively movable parts of the arm system of a person in order to determine said person's aptitude for activity requiring manual dexterity, said apparatus comprising first means for supporting one of the two relatively movable parts, second means for supporting the other of the two parts, at least one of the first and second means being capable of rotation about an axis which substantially coincides with an axis of one degree of freedom of rotational movement of the joint system when the two connected parts are supported in the first and second means, each of the first and second means including means for preventing movement of the respective supported part relative to the first or second means in a direction of decreasing stress on the joint system, third means for applying a constant predetermined force to at least one of the first and second means for biassing the latter to rotate in a direction of increasing stress on the joint system, and fourth means for measuring the static deflection of the joint system resulting from the application of the constant force, the measurement being indicative of the person's aptitude for the given activity.

2. Apparatus according to claim 1 in which both the first and second means are independently rotatable about the axis, and the third means applies the same constant predetermined force to each of the first and second means in opposite directions.

3. Apparatus according to claim 2 in which the first and second means comprise means for supporting adjacent fingers of a hand resectively, the third means comprises means for applying the same constant force to each of the first and second means in opposite directions tending to splay the fingers apart, and the fourth means comprises means for measuring the angle between the first and second means, the apparatus further including means for securing the metacarpal region of the hand against movement.

4. An apparatus according to claim 3 in which the fourth means comprises an angle scale carried by one of the first and second means.

5. An apparatus according to claim 4 further including a rod extending between the two fingers perpendicularly to the plane of the hand and adjustable in a direction along the bisector of the fingers.

6. Apparatus according to claim 1 in which the first means comprises a substantially flat support surface and means to press the metacarpal region of one hand against the flat surface, the second means comprises a member for supporting the four fingers of the hand, said member being hinged relative to the surface for rotation about an axis running through the articular space between the metacarpal bones and the bones of the adjoining finger segments, the third means comprises means for applying a constant predetermined force to the hinged member in a direction which endeavours to bend the fingers back relative to the metacarpal region of the hand, and the fourth means comprises means to measure the angular position of the hinged member.

7. An apparatus according to claim 1 in which the first means comprises a substantially flat surface for supporting the lower arm, palm and four fingers of the arm system, meanns for fixing the wrist and lower arm relative to the surface, and a stop means for locating the outer side of the index finger, the second means comprises a fixture for holding the thumb, said fixture being hinged relative to the flat surface for rotation about an axis which substantially coincides with the axis of rotation of the thumb relative to the index finger, the third means comprises means for applying a constant predetermined force to the fixture in a direction tending to bend the thumb away from the index finger, and the fourth means comprises means for measuringthe angular position of the fixture.

8. Apparatus according to claim 1 in which the first means comprises means for securing the upper arm and elbow against movement, the second means comprises means for clamping the wrist and supporting the lower arm at right angles to the upper arm, the third means comprises means to apply a constant force tending to rotate the lower arm about its own axis, and thefourth means comprises means for measuring the angular orientation of the clamp means.

9. Apparatus according to claim 8 in which the third means comprises a cord pulley.

10. Apparatus according to claim 8 further comprising a sling for supporting the hand.

11. Procedure for testing a joint system between two relatively movable parts of the arm system of a person in order to determine said person's aptitude for an activity requiring manual dexterity, comprising supporting the joint system in a manner allowing one degree of freedom of rotational movement between the two relatively movable parts, restraining one of the two parts against movement in a direction of decreasing stress on the joint system, applying a constant predetermined force to the other of the two parts in a direction of increasing stress on the joint system, and measuring the resultant static deflection of the joint system.

12. Procedure according to claim 11 in which one hand of the person is restrained in the region of the metacarpal bones, a constant predetermined force endeavouring to bend the fingers towards the back of the hand is applied to the four fingers, excluding the thumb, and the resulting angle between the four fingers and the metacarpus is measured.

13. Procedure according to claim 11 in which the four fingers and the metacarpal region of the hand are restrained, a constant predetermined force tending to bend the thumb away from the adjacent index finger is applied, and the angle between the thumb and index finger is measured.

14. Procedure according to claim 11 in which the upper arm and the elbow joint are restrained, a constant predetermined force is applied to the wrist joint tending to rotate the lower arm about its own axis, and the resulting angular orientation of the wrist joint is measured.

15. Procedure for testing a joint system between two relatively movable parts of the arm system of a person in order to determine said person's aptitude for an activity requiring manual dexterity, comprising supporting the joint system in a manner allowing one degree of freedom of rotational movement between the two relatively movable parts, applying equal and opposite constant predetermined forces respectively to the two parts tending to increase the stress on the joint system, and measuring the resultant static deflection of the joint system.

16. Procedure according to claim 15 in which one hand of the person is restrained in the region of the metacarpal bones, equal and opposite constant predetermined forces endeavouring to splay one finger away from an adjoining finger are applied to the fingers and the resulting angle between the two fingers is measured.

17. Procedure for testing the amplitude of movement of a joint system between two connected parts of the arm system of a person in order to determine said person's aptitude for an activity requiring manual dexterity, which procedure comprises the steps of
  holding one of said parts in a stationary position,
  subjecting the other of said parts to a predetermined force acting in the direction of one degree of movement of the joint system, and
  measuring the resultant static deflection of said other part.

* * * * *